(12) United States Patent
Baas et al.

(10) Patent No.: US 10,906,827 B2
(45) Date of Patent: Feb. 2, 2021

(54) SYSTEMS AND METHODS FOR REDUCING ALGAE BLOOMS AND MICROBIAL GROWTH BY PHOSPHORUS REMOVAL FROM AQUEOUS SYSTEMS

(71) Applicants: Koos Jan Baas, Wellington, FL (US); Joris Johannes Brigitta Salden, Noord Brabant (NL)

(72) Inventors: Koos Jan Baas, Wellington, FL (US); Joris Johannes Brigitta Salden, Noord Brabant (NL)

(*) Notice: Subject to any disclaimer, the term of this patent is extended or adjusted under 35 U.S.C. 154(b) by 360 days.

(21) Appl. No.: 15/786,228

(22) Filed: Oct. 17, 2017

(65) Prior Publication Data

US 2018/0111863 A1  Apr. 26, 2018

Related U.S. Application Data

(60) Provisional application No. 62/411,877, filed on Oct. 24, 2016.

(51) Int. Cl.
| | |
|---|---|
| *C02F 3/30* | (2006.01) |
| *C02F 1/58* | (2006.01) |
| *C12N 1/20* | (2006.01) |
| *C02F 1/70* | (2006.01) |
| *C02F 1/42* | (2006.01) |

(Continued)

(52) U.S. Cl.
CPC ............ *C02F 3/308* (2013.01); *C02F 1/42* (2013.01); *C02F 1/58* (2013.01); *C02F 1/70* (2013.01);

(Continued)

(58) Field of Classification Search
CPC ...... C02F 9/00; C02F 1/281; C02F 2101/105; C02F 1/42; C02F 2303/16; C02F 3/308; C02F 3/322

See application file for complete search history.

(56) References Cited

U.S. PATENT DOCUMENTS

| | | | | |
|---|---|---|---|---|
| 3,723,308 A | * | 3/1973 | Breck | ...................... B01J 39/02 210/681 |
| 4,695,387 A | * | 9/1987 | Berry | ...................... B01J 39/14 210/676 |

(Continued)

FOREIGN PATENT DOCUMENTS

WO    WO-2011107524 A1 *  9/2011  ................ C02F 1/42

OTHER PUBLICATIONS

Lee M. Blaney et al., Hybrid anion exhanger for trace phosphate removal from water and wastewater; Elsevier 41 (Science Direct), 2007, pp. 1603-1613. (Year: 2007).*

(Continued)

*Primary Examiner* — Ana M Fortuna
(74) *Attorney, Agent, or Firm* — The Plus IP Firm; Derek Fahey

(57) ABSTRACT

A system for reducing algae blooms and microbial growth in aqueous systems is disclosed. The system includes a phosphates adsorption container having an ingress and an egress and a phosphates adsorption element contained therein for gathering and removing phosphates as phosphates-rich influent water flows through the phosphates adsorption container thereby producing low phosphates concentration effluent water. The system also uses a first solution combining the phosphates gathered from the influent water producing a phosphates-enriched first solution and for restoring high loading capacity for adsorption of phosphates properties and high attraction to phosphates properties of the phosphates adsorption element. The system includes a first solution recovery element for receiving the phosphates-enriched solution and for separating the phosphates from the phosphates-enriched first solution.

19 Claims, 4 Drawing Sheets

(51) Int. Cl.
*C02F 1/00* (2006.01)
*C02F 101/10* (2006.01)
*C02F 103/06* (2006.01)
*C02F 103/02* (2006.01)
*C02F 103/00* (2006.01)
*C12N 1/04* (2006.01)
*C02F 103/10* (2006.01)

(52) U.S. Cl.
CPC ............... *C12N 1/04* (2013.01); *C12N 1/20* (2013.01); *C02F 1/001* (2013.01); *C02F 2101/105* (2013.01); *C02F 2103/001* (2013.01); *C02F 2103/007* (2013.01); *C02F 2103/023* (2013.01); *C02F 2103/06* (2013.01); *C02F 2103/10* (2013.01); *C02F 2209/006* (2013.01); *C02F 2209/008* (2013.01); *C02F 2209/18* (2013.01); *C02F 2209/445* (2013.01); *C02F 2303/04* (2013.01); *C02F 2303/16* (2013.01); *C02F 2303/20* (2013.01); *C02F 2307/14* (2013.01); *Y02W 10/37* (2015.05)

(56) References Cited

U.S. PATENT DOCUMENTS

| | | | | |
|---|---|---|---|---|
| 5,948,265 | A * | 9/1999 | Wakamatsu | B01J 41/10 210/683 |
| 6,171,503 | B1 * | 1/2001 | Cameron | B01J 39/04 210/670 |
| 7,520,987 | B1 * | 4/2009 | Williams | C02F 1/42 210/291 |
| 2007/0275450 | A1 * | 11/2007 | Roberts | C02F 3/28 435/243 |
| 2008/0314830 | A1 * | 12/2008 | Banerjee | C02F 1/5245 210/631 |
| 2013/0098840 | A1 * | 4/2013 | Helferich | C02F 1/281 210/670 |
| 2014/0138320 | A1 * | 5/2014 | Siwek | B01J 20/0281 210/681 |
| 2018/0273401 | A1 * | 9/2018 | SenGupta | C02F 1/42 |

OTHER PUBLICATIONS

Guoren Xu et al. Adsorption and removal Efficiency of inorganic, Polymeric and Organic Phosphates from aqueous Solutions on Biochar Derived From Sewage Sludge or Chemically enhanced Primary Treatment Process; https://www.research. net/publication/6498436_ Hybrid_anion_exchanger_for_trace_Ph (Year: 2018).*

Scott Miracle-Gro, CRS News Oct. 25, 2018 (internet posted date) (https://www.csrwire.com/press_releases/41481-Finalists-Named-in-10-Million-Race-Again . . . ). (Year: 2018).*

* cited by examiner

SYSTEMS AND METHODS FOR REDUCING ALGAE BLOOMS AND MICROBIAL GROWTH BY PHOSPHORUS REMOVAL FROM AQUEOUS SYSTEMS

CROSS-REFERENCE TO RELATED APPLICATIONS

This application claims the benefit of the filing date of U.S. Provisional Application Ser. No. 62,411,877 titled "SYSTEMS AND METHODS TO PREVENT ALGAE BLOOMS AND MICROBIAL GROWTH BY PHOSPHORUS REMOVAL FROM AQUEOUS SYSTEMS" and filed Oct. 24, 2016 and the subject matter of which is incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable

TECHNICAL FIELD

This invention relates to algae blooms or microbial growth in aquatic systems, and more specifically, systems and methods for reducing or limiting algae blooms or microbial growth in aquatic systems.

BACKGROUND

Algae are unicellular or multicellular microorganisms common in aquatic systems. Due to their typically photosynthetic growth, using sunlight and carbon dioxide as primary inputs, algae are considered the base of aquatic food webs and are important to the nutrition of aquatic systems. The abundance and growth of algae are governed by the availability of light, temperature, the number of major nutrients, such as inorganic nitrogen and phosphorus, the number of minor nutrients, such as iron and other trace metals or essential vitamins, and the presence and activity of predators and/or viruses. Additionally, there is a growing scientific consensus about the growth limiting properties of phosphorus in extremely low concentrations.

Algae blooms, which is the mass development of algae that can lead to discoloration of the water, occur in stagnant or slowly flowing waters. Algae blooms occur usually as a consequence of or related to higher water temperatures, sunlight, and elevated phosphorus and nitrogen concentrations. Some algae blooms can be part of a natural seasonal succession in a given aquatic ecosystem. But many algae blooms have been linked to the excess input of nitrogen and phosphorus compounds into the waters, mainly from urban pollution or agricultural fertilizer runoff.

Algae blooms can cause severe damage to the ecosystem's function and to human health and can have intense economic impact. Such blooms are then termed "harmful algae blooms" or HAB. At first, HAB leads to visible discoloration of the water, which can negatively affect bottom-dwelling algae and plants, such as seagrass, by limiting the light reaching the bottom. These impacts can have wider cascading effects in the ecosystem.

Algae blooms can also cause harm and economic impact by the production of toxins. Toxins, which are not toxic to aquatic invertebrates, such as clams and shellfish, and fish, accumulate in the food chain and cause health problems when consumed by human. Human health effects can comprise gastrointestinal and neurological problems, ranging from stomach aches to temporary or permanent cognitive and other neurological damage, kidney failure, heart arrest, and death. Toxic HABs can also affect aquatic mammals, such as manatees, and contact with HAB-laden lake water has been known to cause death in cows and dogs.

Economic impacts from HAB can originate from the closure of fishing grounds and clam or oyster beds due to toxin accumulation in harvested seafood, from loss of fish stocks as a result of hypoxia, or from negative effects on tourism caused by health concerns and the unsightly discoloration and smell of algae blooms in recreational waters.

Algae blooms will, in most but not all cases, usually subside after a while and the ecosystem returns to a "normal" state. As most HAB are related to excessive nitrogen and/or phosphorus concentrations in the water originating from human activities, however, in most cases the algae blooms will re-occur annually, or at other intervals, if the environmental conditions and practices, namely the input of nitrogen and/or phosphorus compounds, remain unchanged.

Phosphorus plays a major role in the structural framework of DNA and RNA. Living cells use phosphate to transport cellular energy in the form of adenosine triphosphate (ATP). ATP is also essential for the key regulatory cell process of phosphorylation. Phospholipids are the main structural components of cell membranes. Since phosphorus is required for all forms of life, phosphorus removal from the water to very low concentrations is an effective measure to prevent microbial and algae growth in such waters.

Phosphorus removal or reduction is, therefore, a feasible venue to mitigate algae blooms. Such mitigation can occur through effective phosphorus removal within the natural body of water, or by processing natural surface water to remove the phosphorus. Or mitigation can intercept phosphorus sources before they reach natural surface waters; for example, as a final treatment step in wastewater or storm water treatment prior to discharge to natural bodies of water, or as a treatment of agricultural, industrial, or urban water runoff prior to reaching natural bodies of water.

Since the limitation of growth under complete or severe phosphorus removal applies not only to algae but to all aquatic microorganisms, phosphorus removal is also an effective venue to prevent microbial growth, including bacterial growth, in water systems including, but not limited to water-driven cooling systems, water storage and distribution systems, or water treatment systems, such as reverse osmosis and desalination systems. In such systems, microbial growth can form a biofilm, a layer of microorganisms usually embedded in a matrix of various organic compounds, a process called biofouling. Biofouling can interfere with the functioning of water treatment, storage, or cooling systems or with further water processing and treatment.

Several methods for the removal of phosphate by formation and precipitation of iron or metal complexes and the subsequent removal of such precipitates by typically filtration methods are known in the art. Several methods for the removal and precipitation of phosphate using calcium compounds and changes of pH are known to the art. Other methods known to the art include absorption or adsorption of phosphate to various matrices. Some methods of phosphate removal from aqueous solutions using a biological enzyme, ferritin, are known to the art. Several methods of removing phosphate from water by use of specific or unspecific ion exchange resins are known in the art.

However, for the purpose of algae bloom control and microbial growth prevention, the methods disclosed in the art have various shortcomings that render those inventions technically or economically infeasible or at least difficult at large and commercial scales.

As a result, there exists a need in the art for a system and method for removing phosphates from water to very low effluent concentrations while providing a method for capture and reuse of removed phosphates, for providing such a system and method for an economically feasible cost, and for doing so for high water volumes and/or flow rates.

SUMMARY

Systems and methods for preventing algae blooms and microbial growth in aqueous systems are disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, system for reducing algae blooms and microbial growth in aqueous systems are disclosed. The system includes at least one phosphates adsorption container having an ingress and an egress. A phosphates adsorption element contained within the phosphates adsorption container gathers a plurality of phosphates and removes said phosphates as said phosphates-rich influent water flows through the phosphates adsorption container thereby producing low phosphates concentration effluent water. The system also uses a first solution for combining with said phosphates gathered from the influent water producing a phosphates-enriched first solution and for restoring high loading capacity for adsorption of phosphates properties and high attraction to phosphates properties of the phosphates adsorption element. The system also includes a first solution recovery element for receiving the phosphates-enriched first solution and for separating the phosphates from the phosphates-enriched first solution thereby allowing the first solution to be reused.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. The embodiments illustrated herein are presently preferred, it being understood, however, that the invention is not limited to the precise arrangements and instrumentalities shown, wherein.

DETAILED DESCRIPTION

Figure 1:
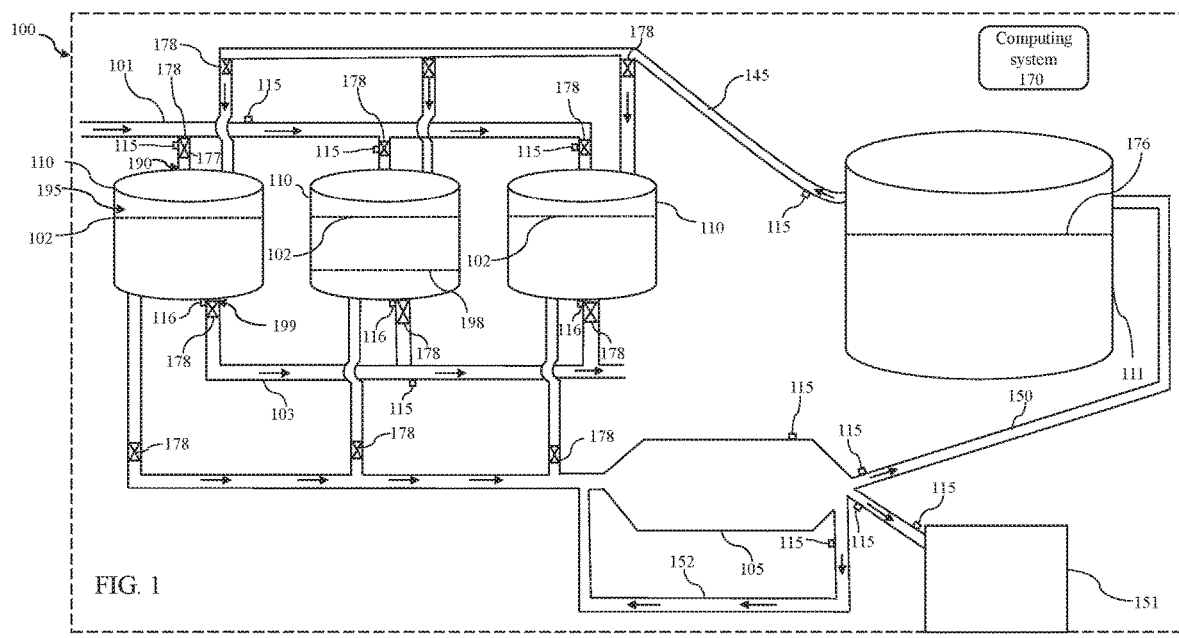
FIG. 1 is a block diagram illustrating the main components of the system for reducing algae blooms and microbial growth in aqueous systems, according to an example embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting, reordering, or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a system that reduces algae blooms and microbial growth in aqueous systems. It is understood that the term "reduces" used throughout the application also means to reduce to zero or to prevent blooms and microbial growth in aqueous systems. The system is an improvement over the prior art in that it reduces algae blooms and microbial growth by achieving very low phosphorus concentrations at large scale and high throughput at an economically feasible cost. The system does so by providing a system that reduces phosphates to effluent concentrations of less than 10 parts per billion ("ppb"), which is accomplished by adsorption of phosphates (or phosphorus-containing substances) out of the treated water by a phosphates adsorption in a water treatment system that allows high throughput processing of water and achievement of very low effluent phosphorus concentrations.

The present invention also improves over the prior art by removing phosphates from water fractions with a phosphates adsorption element that is specifically capable of phosphates adsorption and has a high affinity and high binding capacity. The system is also capable of regenerating said a phosphates adsorption element with a first solution or an alkaline regeneration solution and collecting the phosphates-enriched first solution and to precipitate the phosphates into a brine that is separated from first solution or the regeneration solution, which can be reused, while the phosphates are recaptured from the brine for later reuse as fertilizer or in other appropriate applications.

As used herein, the terms "aquatic system" and "aqueous system" shall comprise any system or body of water, including, but not limited to, natural and artificial surface waters, such as a lake, a pond, a pool, a reservoir, a manure pit, a spring, a creek, a river, a stream, an estuary, a bay or lagoon, a tidal or intertidal area, a marsh, a swamp, a sea or an ocean; as well as non-surface waters, such as groundwater, well water, an aquifer, a natural or man-made water distribution system; and, as well as municipal and industrial wastewater, storm water, effluent from a water or sewage treatment plant, agricultural runoff, acid mine drainage, sludge, and cooling water.

As used herein, the term "algae" shall comprise all organisms described as eukaryotic, phototrophic (i.e., performing and living exclusively or partially off photosynthesis) protists, comprising, but not limited to, members of the biological classifications of Euglenophyta, Cryptophyta, Prymnesiophyta, Dinophyta (Pyrrhophyta), Ochrophyta (including diatoms), Raphidiophyta, Chrysophyta, Synurophycea, Phaeophyta, Rhodophyta, and Chlorophyta; and all organisms described as prokaryotic cyanobacteria (syn. Cyanophyta, blue-green algae).

As used herein, the term "algae bloom" refers to a mass development of algae, as defined above, in natural or artificial surface waters or other at least temporarily illuminated waters, whereby the high abundance of said algae can lead to a visible discoloration of the water, said discoloration being typically of greenish, reddish, yellowish to orange, brownish, or whitish/gray appearance.

As used herein, the term "microbial growth" refers to the growth of any microbial organism, or microorganism, including bacteria, cyanobacteria, algae, other protists (e.g., ciliates, flagellates, amoeba), and fungi.

As used herein, the term "phosphate" refers to the inorganic form of phosphorus characterized by the possession of a PO4 group, whether as PO4, HPO4, or H2PO4, occurring in ionic form when dissolved in water.

As used herein, the term "phosphates" refers to the cumulative of all inorganic phosphates, including orthophosphate and polyphosphate, and organic phosphates, such as but not limited to phosphonate.

As used herein, the term "dissolved phosphates" refers to all phosphates, as defined above, that are physically dissolved in the water or in a colloidal form small enough to pass through a 0.2 µm pore-size polycarbonate membrane filter; following the practical definition of "dissolved" as used in the art of aquatic sciences.

As used herein, the term "MGD" refers to the flow unit of "mega-gallons per day," or one million gallons per day; equivalent to 694.4 gallons per minute (gpm), or 3785.4 m3 per day, or 157.7 m3 per hour.

As used herein, the term "about" means approximately, in the region of, roughly, or around. When the term "about" is used in conjunction with a numerical value or range, it modifies that value or range by extending the boundaries above and below the numerical value(s) set forth within a confidence interval of 90%.

Figure 2:
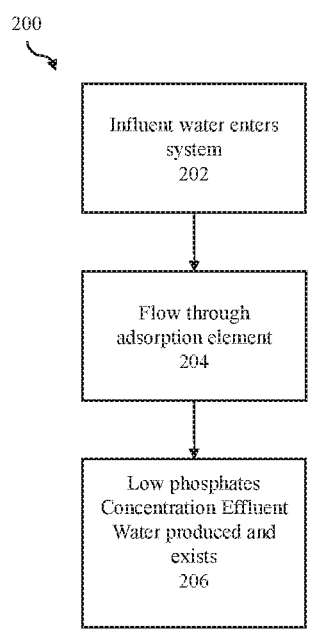
FIG. 2 is a flowchart describing certain steps of one of the processes performed by the system, according to an example embodiment.
Figure 3:
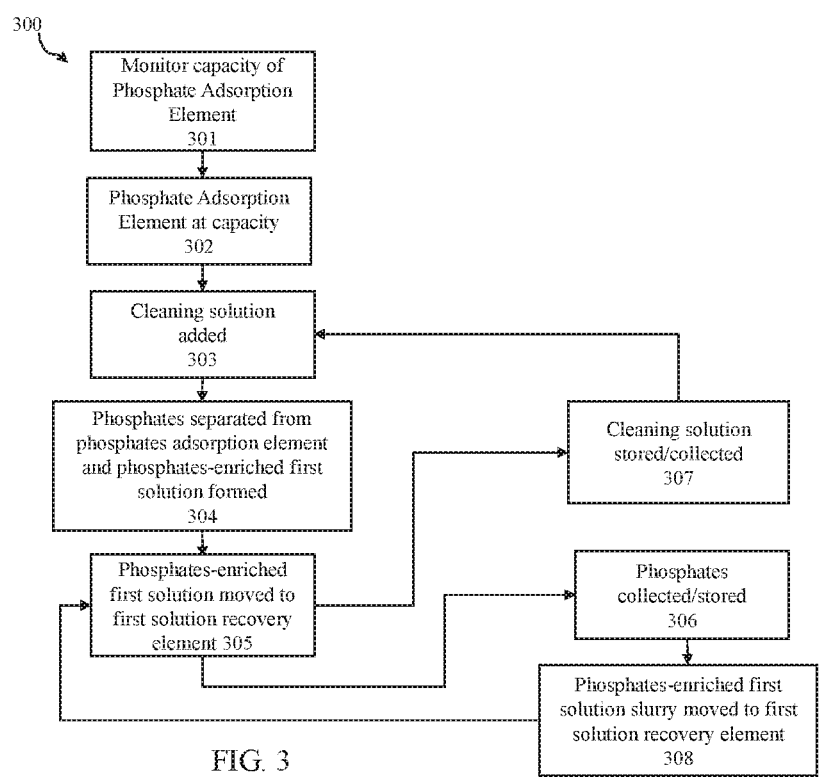
FIG. 3 is a second flowchart describing certain steps of one of the processes performed by the system, according to an example embodiment; and, FIG. 4 is a block diagram of a system including an example computing device and other computing devices, according to an example embodiment.

Referring now to the Figures, FIGS. 1-3 will be discussed together. FIG. 1 is a block diagram illustrating the main components of the system 100 for reducing algae blooms and microbial growth in aqueous systems, according to an example embodiment. The system is configured to produce effluent water leaving the system having concentrations of phosphates below a threshold phosphates concentration to limit development of algae blooms and microbial growth. In one embodiment, the threshold phosphates concentration may be 20 ppb, 10 ppb or 5 ppb. The threshold phosphates concentration may be adjusted depending on a variety of factors.

The system 100 includes at least one phosphates adsorption container having an ingress 190 and an egress 199. In one embodiment, the container is a free-standing tank or another vessel or container, well known to those skilled in the art. However, other types of containers or containments or flow through systems for containing fluids may also be used and are within the spirit and scope of the present invention. In one embodiment, the phosphates adsorption container comprises at least one 10 ft. by 10 ft. tank for processing a million gallons per day (MGD). The system may include multiple phosphates adsorption containers as illustrated in FIG. 1, which will be further explained below.

Each phosphates adsorption container can be made of plastics, such as HDPE, LDPE, polycarbonate, acrylic, PTFT, or any other suitable polymer, or of glass, (stainless) steel, other metal, concrete, or any material providing long-term stability in an aqueous application and is compatible with alkaline solutions or a clay or lined sand bed.

The system also includes a phosphates adsorption element 102 housed within the phosphates adsorption container. The phosphates adsorption element is for gathering a plurality of phosphates and for removing said phosphates as said phosphates-rich influent water flows through the phosphates adsorption container thereby producing low phosphates concentration effluent water. The phosphates adsorption element may comprise a BioPhree® (Ion exchange resin containg iron oxide, from Green Water Solution, Inc.) material 102. In one embodiment, the phosphates adsorption container may not be completely filled with the BioPhree® (Ion exchange resin containg iron oxide, from Green Water Solution, Inc.) material or P adsorption resin. The phosphates adsorption element comprises a high affinity or attraction to phosphates and a high loading capacity for phosphates such that when said phosphates-rich influent water flows through the at least one phosphates adsorption container and the phosphates adsorption element, the system thereby produces low phosphates concentration effluent water and gathers phosphates from the phosphates-rich influent water. In one non-limiting embodiment, the phosphates adsorption element may be an ion exchange resin material, such as BioPhree® (Ion exchange resin containg iron oxide, from Green Water Solution, Inc. ) or any other specific brand of ion exchange resin with suitable specifications. BioPhree® (Ion exchange resin containing iron oxide, from Green Water Solution, Inc.) or ion exchange resin material has a high affinity to phosphates and a high loading capacity for phosphates such that when said influent water flows through the at least one phosphates adsorption containment having the phosphates adsorption element, the system thereby produces low phosphates concentration effluent water and gathering phosphates from the phosphates-rich influent water.

In one embodiment the phosphates adsorption element may comprises a bed of BioPhree® (Ion exchange resin containing iron oxide, from Green Water Solution, Inc.) or phosphates adsorption element having a 3 ft. bed height within the 10 ft. by 10 ft. phosphates adsorption container. In such an embodiment, a head space 195 above the bed of phosphates adsorption element allows for even distribution of incoming influent water over the whole surface of the phosphates adsorption element. In another embodiment, additional sections or layers having different compositions may also be used and are within the spirit and scope of the present invention. For example, the additional sections 198 may include either a "hollow" space underneath a solid, perforated support plate holding the phosphates adsorption element, or a layer of a pebble and sand bed, which will prevent the wash-out of the phosphates adsorption element from the tank. However, other types of materials for adsorption of phosphates may also be used and are within the spirit and scope of the present invention.

The system may also include a first solution or regeneration solution 176 for combining with said phosphates gathered from the influent water producing a phosphates-enriched first solution. The first solution also has properties capable of restoring high loading capacity for adsorption of phosphates properties and high attraction to phosphates properties of the phosphates adsorption element. In one embodiment the first solution is stored separate from the phosphates adsorption container in a first container 111. In one non-limiting embodiment, the regeneration or first solution is an alkaline solution, such as a 3% sodium hydroxide or a 3% potassium hydroxide solution in water. In another embodiment the alkaline solution may comprise a sodium hydroxide or potassium hydroxide solution of less than 10% concentration. The regeneration or first solution desorbs the phosphates from the ion exchange resin or phosphates adsorption element, creating a phosphates-enriched regeneration solution or a phosphates-enriched first solution. In one embodiment, a volume of first solution of no more than about three times a volume of said phosphates adsorption element is required for restoring said high loading capacity for adsorption of phosphates properties and high attraction to phosphates properties of said phosphates adsorption element. In one embodiment, a volume of first solution or regeneration solution about two times a volume of said phosphates adsorption element is required for restoring said high loading capacity for adsorption of phosphates properties and high attraction to phosphates properties of said phosphates adsorption element.

In operation, in step 202, phosphates-rich influent water enters into the system. In one embodiment, the influent water enters the system via a conduit 101 or multiple of conduits at a first end of the system. In one embodiment a sand filter, or another suitable high-throughput filter bed, may be installed upstream of the water treatment containment to eliminate particles from the water stream. The influent water entering the system will be phosphates-rich influent water from an aqueous system. The phosphates-rich influent water entering the system may have a cumulative phosphates content of at least 20 parts per billion ("ppb-P"), in particular at least 100 ppb-P, more in particular at least 200 ppb-P. In principal, there is no upper limit of the phosphates content a water fraction to be treated can have, and the maximum for the phosphates content is not critical for the disclosed method; however, a suitable practical upper limit for the method may be at most 50,000 ppb-P (50 ppm-P). At concentrations of 50 ppm-P, classic P removal technologies may be more suitable.

As the water enters the system, water moves from conduits 101 and into at least one phosphates adsorption container 110 through secondary influent water conduits 177. In one embodiment, the system may also include valve or a system of valves or gates 178 to control in which phosphates adsorption container the phosphates-rich influent water enters. The valves or system of valves may be used to isolate one or more phosphates adsorption containers so that the phosphates adsorption elements within one or more phosphates adsorption containers may be regenerated or restored (further explained below) while allowing the system to function and continue to produce low phosphates concentration effluent water.

Next, in step 204, after the phosphates-rich influent water is received into each operating phosphates adsorption container and passes through the phosphates adsorption element exiting the phosphates adsorption container's egress 199. The phosphates adsorption element has a high affinity or attraction to phosphates properties and has a high capacity of being loaded with phosphates. As the phosphates-rich influent water flows through or interacts with the phosphates adsorption element, the high attraction to phosphates properties and high capacity of being loaded with phosphates properties of the phosphates adsorption element gathers phosphates from the phosphates-rich influent water and adsorbs phosphates thereby producing low phosphates concentration effluent water that exit through the egress 199.

In one embodiment, the low phosphates concentration effluent water is below a threshold phosphates concentration thereby reducing development of algae blooms and microbial growth. In one embodiment, the threshold phosphates concentration in the effluent water is less than 10 ppb-P. However, the threshold phosphates concentration may also be may be less than 5 ppb-P. The threshold phosphates concentration may be adjusted depending on a variety of factors.

In step 206, the low phosphates concentration effluent water leaves the system. The low phosphates concentration effluent water exits the system though a conduit or series of conduits 103. While only one conduit 103 is illustrated it is understood that multiple conduits may be used and is within the spin and scope of the present invention. Treated low concentration effluent water exits the phosphorus adsorption containment and is released from the system.

Water treatment by and through the at least one phosphates adsorption container can continue up to the phosphates loading capacity of the phosphates adsorption element, after which the flow of influent water flow into the system may be stopped by appropriate valves 178. In systems comprising multiple phosphorus adsorption containers, operation shall be timed such that the different phosphates adsorption element 102 within each phosphates adsorption container 110 reach the loading capacity of the phosphates adsorption element at different time points. In one embodiment, the system may time the system such that each phosphates adsorption element reaches its capacity at least 24 hours apart. However, other timing sequences are within the spirit and scope of the present invention. Such operation ensures continued operation of the overall water treatment system, while individual phosphates adsorption elements can be regenerated. Valves 178 for controlling the flow of fluid into and out of each of the phosphates adsorption containers so that the when a phosphates adsorption element within one of the phosphates adsorption containers is fully loaded the valves may be used to isolate the fully loaded phosphates adsorption element within the phosphates adsorption container so that the phosphates adsorption element may be regenerated without disrupting the entire system.

Process 300 describes the process for using a first solution 176 for combining with said phosphates gathered from the influent water producing a phosphates-enriched first solution and for restoring high loading capacity for adsorption of phosphates properties and high attraction to phosphates properties of the phosphates adsorption element. In step 301, the system continuously monitors the phosphate concentration in the effluent water using sensors 116 for monitoring phosphates concentration. Such sensors may include chemical sensors, sampling of the effluent water, optical sensors, Raman spectroscopy, reflectance spectroscopy, electrochemical sensors, and biological sensors. However, other types of sensors used for monitoring concentration levels of phosphates are within the spirit and scope of the present invention. In another embodiment, the system may monitor phosphates concentrations of the treatment water intake or ingress of the system and computing the cumulative phosphates loading onto the phosphates adsorption element by multiplying with the measured or adjusted water flow rate, under knowledge of the loading capacity of the specific phosphates adsorption element.

In step 302, the system determines that the phosphates adsorption element has reached its loading capacity by either the monitoring of the phosphates concentration in the effluent water leaving the system by using sensors 116, which will begin to increase above the desired threshold phosphates concentration, upon reaching the loading capacity, or by actual monitoring of the phosphates adsorption element.

The size and geometry of the treatment containment or phosphates adsorption container and phosphates adsorption element can be adjusted to the required through flow, the original phosphates load of the treatment water, spatial constraints of the treatment facility/site, or other preferences subject to optimization. However, it is understood that more than one phosphates adsorption containment may also be used and is within the spirit and scope of the present invention is illustrated in FIG. 3.

The specific embodiment of the release of the effluent water (step 206) will depend on the specific purpose of the water treatment and may comprise a release into the source body of water downstream of the water intake site, such as in a surface water, or into a water containment system (pond, pool, storage tank), or into a water distribution system, or into an installation of water use, such as a cooling system loop, or into any other outlet suitable for the purpose of the water treatment.

The system also includes a first solution stored in a first solution container 111. In one embodiment, the cleaning solution or first solution comprises an alkaline solution as explained above. The size, geometry and form of the first solution container can be adjusted to a variety of spatial constraints of the treatment facility/site, or other preferences subject to optimization. In one embodiment, the first solution volume is not more than three times the phosphates adsorption element of the phosphates adsorption container. In another embodiment, the first solution volume is two times the phosphates adsorption element volume of phosphorus adsorption container. In one embodiment, the first solution is housed within a single first solution container, as illustrated in FIG. 1, however it is understood that more solutions may also be used in or within the spirit and scope of the present invention. The first solution is for combining with said phosphates gathered from the phosphates-rich influent water.

Next, in step 303, the first solution is then moved via the at least one conduit 145 to via a conduit or series of conduits from the first solution container to the phosphates adsorption element. While only one conduit 145 is illustrated it is understood that multiple conduits may be used and is within the spirt and scope of the present invention. In the present embodiment, the regeneration or first solution 176 is pumped from the first container 111 counter-current to the usual treatment water flow direction via at least one conduits 145 through the phosphates adsorption element (step 302). However, in other embodiments, the direction of the flow of the first solution through the phosphates adsorption element is not counter-current. Next, in step 304, as the first solution is pumped through the phosphates adsorption container and through the phosphates adsorption element having phosphates gathered and adsorbed. As the first solution passes through the phosphates adsorption element, the first solution desorbs the phosphates from the adsorption element forming a phosphates-enriched first solution. As the first solution desorbs the phosphates from the phosphates adsorption element, the phosphates adsorption element is regenerated or restored s high loading capacity for adsorption of phosphates properties and high attraction to phosphates properties.

Next, in step 305, the phosphates-enriched first solution is moved to the first solution recovery element. In the first solution recovery element, the desorbed phosphates precipitate out of the phosphates-enriched first solution leaving the phosphates for collection and storage in a tank or container 151 for storage as illustrated in step 306. The phosphates are separated from the first solution to recover the captured phosphates for later reuse. Passive separation through sedimentation of the phosphates precipitates in a flow-through system or tank 105 is one venue of separation. Additionally, nanofiltration may also be used to precipitate out the phosphates from the phosphates-enriched first solution. However, other means are also within the spirit and scope of the present invention. Additionally, after separation, the remaining first solution, now having the phosphates removed, in step 307, can be pumped back to the first solution container 110 via conduits 150 for reuse at a later time for further use in future regeneration cycles. While only one conduit 150 is illustrated it is understood that multiple containment and conduits 150 may be used and is within the spin and scope of the present invention. Additionally, as illustrated in step 308, any slurry of first solution that is not fully separated from phosphates can be re-pumped back, via conduits 152 back through the separation flow-through system or tanks until the phosphates have completely been removed from the first solution.

The system comprises appropriate piping networks, valves 178, valve controllers, and pumps to isolate elements of the system and move treatment water through the phosphates adsorption element and to move the first solution or regeneration solution from the first solution container through the phosphates adsorption element into the collection and separation tank(s) and into the regeneration solution tank. The system may also include a plurality of sensors 115, 116 or probes that monitor the phosphate concentration in each stage of the system. Such sensors may include chemical sensors, sampling of the effluent water, optical sensors, Raman spectroscopy, reflectance spectroscopy, electrochemical sensors, and biological sensors. However, other types of sensors used for monitoring concentration levels of phosphates are within the spirit and scope of the present invention. These sensors may also monitor flow rate, phosphate concentration, first solution flow rate, first solution level, influent water level, effluent water level, effluent flow rate, influent water flor rate etc. The system may also include at least one computing system 170 or processor for processing data received by said sensors and for sending commands to different components of the system.

Figure 4:
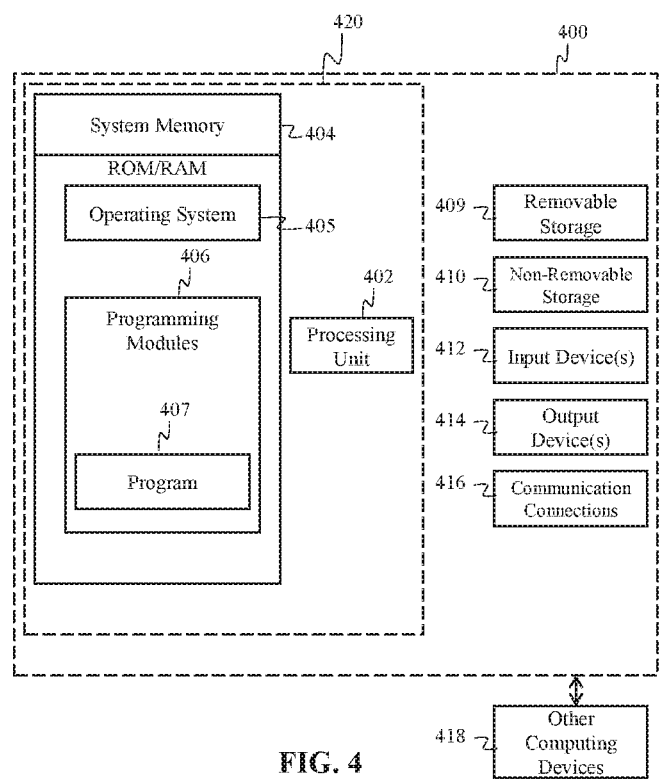

FIG. 4 is a block diagram of a system including an example computing device 400 and other computing devices. Consistent with the embodiments described herein, the aforementioned actions performed by the computing system 170 or computer processor configured to receive a plurality of data from sensors 115, 116 or valves or valve controllers 178 positioned within the system may be implemented in a computing device, such as the computing device 400 of FIG. 4. Any suitable combination of hardware, software, or firmware may be used to implement the computing device 400. The aforementioned system, device, and processors are examples and other systems, devices, and processors may comprise the aforementioned computing device. Furthermore, computing device 400 may comprise an operating environment for the method and process shown in FIGS. 2 and 3 above.

With reference to FIG. 4, a system consistent with an embodiment of the invention may include a plurality of computing devices, such as computing device 400. In a basic configuration, computing device 400 may include at least one processing unit 402 and a system memory 404. Depending on the configuration and type of computing device, system memory 404 may comprise, but is not limited to, volatile (e.g. random access memory (RAM)), non-volatile (e.g. read-only memory (ROM)), flash memory, or any combination or memory. System memory 404 may include operating system 405, one or more programming modules 406 (such as program module 407). Operating system 405, for example, may be suitable for controlling computing device 400's operation. In one embodiment, programming modules 406 may include, for example, a program module 407. Furthermore, embodiments of the invention may be practiced in conjunction with a graphics library, other operating systems, or any other application program and is not limited to any particular application or system. This basic configuration is illustrated in FIG. 4 by those components within a dashed line 420.

Computing device 400 may have additional features or functionality. For example, computing device 400 may also include additional data storage devices (removable and/or non-removable) such as, for example, magnetic disks, optical disks, or tape. Such additional storage is illustrated in FIG. 4 by a removable storage 409 and a non-removable storage 410. Computer storage media may include volatile and nonvolatile, removable and non-removable media implemented in any method or technology for storage of information, such as computer readable instructions, data structures, program modules, or other data. System memory 404, removable storage 409, and non-removable storage 410 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 400. Any such computer storage media may be part of device 400. Computing device 400 may also have input device(s) 412 such as a keyboard, a mouse, a pen, a sound input device, a camera, a touch input device, etc. Output device(s) 414 such as a display, speakers, a printer, etc. may also be included. The aforementioned devices are only examples, and other devices may be added or substituted.

Computing device 400 may also contain a communication connection 416 that may allow device 400 to communicate with other computing devices 418, such as over a network in a distributed computing environment, for example, an intranet or the Internet. Communication connection 416 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

The term computer readable media as used herein may include both computer storage media and communication media.

As stated above, a number of program modules and data files may be stored in system memory 404, including operating system 405. While executing on processing unit 402, programming modules 406 may perform processes including, for example, one or more of the methods or system 100 shown in FIGS. 1-3 above. Computing device 402 may also include a graphics processing unit 403, which supplements the processing capabilities of processor 402 and which may execute programming modules 506, including all or a portion of those systems, processes and methods shown in FIGS. 1-3 above. The aforementioned processes are examples, and processing units 402, 403 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A system for reducing algae blooms and microbial growth in aqueous systems comprising:
    at least one phosphates adsorption container having an ingress and an egress and for receiving phosphates-rich influent water first entering the system;
    a phosphates adsorption element contained within the at least one phosphates adsorption container before the phosphates-rich influent water is received by the system for passively gathering a plurality of phosphates and for removing said phosphates as said phosphates-rich influent water flows through the phosphates adsorption container thereby producing low phosphates concentration effluent water;
    a first solution initially stored in a first solution container separate from the phosphates adsorption container for subsequently combining, within the least one phosphates adsorption container, with said phosphates passively gathered from the influent water by the phosphates adsorption element producing a phosphates-enriched first solution and for restoring high loading capacity for adsorption of phosphates properties and high attraction to phosphates properties of the phosphates adsorption element
    a first solution recovery element connected to the phosphates adsorption container by a conduit for receiving the phosphates-enriched solution and for separating the phosphates from the phosphates-enriched first solution;
    a first return conduit for moving any phosphates-enriched first solution not fully separated from phosphates back into the first solution recovery element for further separating the phosphates from the phosphates-enriched first solution;
    a phosphates collection container connected to the first solution recovery element for collecting phosphates separated from the phosphates-enriched first solution; and,
    a second return conduit directly connected to the first solution container for returning first solution after phosphates are separated from the phosphates-enriched first solution.

2. The system for reducing algae blooms and microbial growth in aqueous systems of claim 1, wherein the low phosphates concentration effluent water is below a threshold phosphates concentration thereby reducing development of algae blooms and microbial growth.

3. The system for reducing algae blooms and microbial growth in aqueous systems of claim 1, wherein the phosphates adsorption element comprises a BIOPHREE ® ion exchange resin having a high efficiency for phosphate material.

4. The system for reducing algae blooms and microbial growth in aqueous systems of claim 1, wherein a volume of first solution of no more than about three times a volume of said phosphates adsorption element is required for restoring said high loading capacity for adsorption of phosphates properties and high attraction to phosphates properties of said phosphates adsorption element.

5. The system for reducing algae blooms and microbial growth in aqueous systems of claim 1, wherein a volume of first solution about two times a volume of said phosphates adsorption element is required for restoring said high loading capacity for adsorption of phosphates properties and high attraction to phosphates properties of said phosphates adsorption element.

6. The system for reducing algae blooms and microbial growth in aqueous systems of claim 1, wherein the phosphates then desorbed into and forming the phosphate-enriched first solution is separated from said first solution by a separation process such that said first solution can be re-used.

7. The system for reducing algae blooms and microbial growth in aqueous systems of claim 1, wherein the threshold phosphates concentration in the effluent water is less than 10 ppb-P.

8. The system for preventing algae blooms and microbial growth in aqueous systems of claim 1, wherein the first solution comprises an alkaline solution.

9. The system for preventing algae blooms and microbial growth in aqueous systems of claim 8, wherein the alkaline solution comprises at least one of a sodium hydroxide or potassium hydroxide solution of less than 10% concentration.

10. A system for reducing algae blooms and microbial growth in aqueous systems comprising:
    at least one phosphates adsorption container having an ingress for receiving phosphates-rich influent water first entering the system and an egress; and,
    a phosphates adsorption element contained within the phosphates adsorption container before the phosphates-rich influent water is received by the system for gathering a plurality of phosphates and for removing said phosphates from phosphates-rich influent water as said phosphates-rich influent water flows through the phosphates adsorption container thereby producing low phosphates concentration effluent water that exit the egress having a threshold phosphates concentration of less than about 5 ppb-P;
    a first solution recovery element connected to the phosphates adsorption container by a conduit for receiving the phosphates-enriched solution and for separating the phosphates from the phosphates-enriched first solution;
    a first return conduit for moving any phosphates-enriched first solution not fully separated from phosphates back into the first solution recovery element for further separating the phosphates from the phosphates-enriched first solution;
    a phosphates collection container connected to the first solution recovery element for collecting phosphates separated from the phosphates-enriched first solution; and,
    a second return conduit directly connected to the first solution container for returning first solution after phosphates are separated from the phosphates-enriched first solution.

11. The system for reducing algae blooms and microbial growth in aqueous systems of claim 10, wherein the phosphates adsorption element comprises high attraction to phosphates properties and high loading capacity for adsorption of phosphates properties.

12. The system for reducing algae blooms and microbial growth in aqueous systems of claim 11, wherein the phosphates adsorption element comprises a BIOPHREE® ion exchange resin having a high efficiency for phosphate material.

13. The system for reducing algae blooms and microbial growth in aqueous systems of claim 10, wherein the system further includes a first solution initially stored in a first solution container separate from the phosphates adsorption container for subsequently combining with said phosphates gathered from the influent water by the adsorption element producing a phosphates-enriched first solution and for restoring said high attraction to phosphates properties and high loading capacity for adsorption of phosphates properties of the phosphates adsorption element.

14. The system for preventing algae blooms and microbial growth in aqueous systems of claim 13, wherein the first solution comprises an alkaline solution.

15. A method for reducing algae blooms and microbial growth in aqueous systems comprising:
receiving phosphates-rich influent water having a plurality of phosphates within at least one phosphates adsorption container having an ingress and an egress;
producing low phosphates concentration effluent water from the influent water flowing through the phosphates adsorption container by causing said influent water to interact with a phosphates adsorption element;
restoring high loading capacity for adsorption of phosphates properties and high attraction to phosphates properties of the phosphates adsorption element and producing a phosphates-enriched first solution by combining a first solution from a first solution container separate from the phosphates adsorption container with the phosphates gathered by the phosphates adsorption element from the influent water;
moving the phosphates-enriched first solution to at least one first solution recovery element for separating phosphates from the phosphates-enriched first solution by a separation process such that said first solution can be re-used
moving phosphates-enriched first solution not fully separated from phosphates back into the first solution recovery element through a first return conduit for further separating the phosphates from the phosphates-enriched first solution;
collecting phosphates separated from the phosphates-enriched first solution in a phosphates collection container that is separate from the first solution recovery element;
returning to the first solution container the first solution after the phosphates are separated from the phosphates-enriched first solution.

16. The method for reducing algae blooms and microbial growth in aqueous systems of claim 15, wherein the threshold phosphates concentration in the effluent water is less than about 10 ppb-P.

17. The method for reducing algae blooms and microbial growth in aqueous systems of claim 15, wherein the phosphates adsorption element comprises a BIOPHREE ® ion exchange resin having a high efficiency for phosphate material.

18. The method for reducing algae blooms and microbial growth in aqueous systems of claim 15, wherein a volume of first solution of no more than about three times a volume of said phosphates adsorption element is required for restoring said high loading capacity for adsorption of phosphates properties and high attraction to phosphates properties of said phosphates adsorption element.

19. The method for reducing algae blooms and microbial growth in aqueous systems of claim 15, wherein a volume of first solution about two times a volume of said phosphates adsorption element is required for restoring said high loading capacity for adsorption of phosphates properties and high attraction to phosphates properties of said phosphates adsorption element.

* * * * *